United States Patent [19]

Liu

[11] Patent Number: 4,808,629

[45] Date of Patent: Feb. 28, 1989

[54] SAFE ANTILEUKEMIA DRUG, SAL

[76] Inventor: Yaguang Liu, 30 Seaman Ave., #4A, New York, N.Y. 10034

[21] Appl. No.: 62,073

[22] Filed: May 14, 1987

Related U.S. Application Data

[62] Division of Ser. No. 737.949, May 28, 1985, Pat. No. 4,675,318.

[51] Int. Cl.4 .................... A61K 31/19; A61K 31/015
[52] U.S. Cl. ..................................... 514/557; 514/766; 514/885
[58] Field of Search ........................ 514/557, 766, 885

[56] References Cited

U.S. PATENT DOCUMENTS 4,033,818 7/1977 Pourrat et al. .................. 424/195.1

OTHER PUBLICATIONS

Chem. Abst. 83:15471s, 1987.
Merck Index, 9th ed., No. 6673, p. 887, 1976.

Primary Examiner—John W. Rollins
Attorney, Agent, or Firm—Chenpatents

[57] ABSTRACT

A new pharmaceutical composition for treating non-lymphatic leukemia, such as granulocytic and monocytic leukemia comprising Harringtonine, Homoharringtonine, Anethole, Oleanolic acid and Ginsenoside and method of making the same.

2 Claims, No Drawings

SAFE ANTILEUKEMIA DRUG, SAL

This application is a division, of application Ser. No. 737,949, filed May 28, 1985, now U.S. Pat. No. 4,675,318.

BACKGROUND OF THE INVENTION

1. Field of the Invention

This invention relates to a new pharmaceutical composition for treating leukemia, more specifically, for treating nonlymphatic leukemia, such as acute chronic granulocytic and monocytic leukemia without adverse side effects.

2. Description of the Prior Art

Numerous antileukemia drugs have been investigated but so far, there is no single drug that is effective and safe. As discussed in U.S. Pat. No. 3,497,593, an alkaloid from Tylophora plant is said to have antitumor activity against mouse leukemia (L-1210). U.S. Pat. No. 3,928,584 disclosed an organic composition derived from tree saps and is said to have activity against mouse leukemia P-388. Also U.S. Pat. No. 4,431,639 disclosed that an extract of Rhisoma Stractylis promotes the production of lymphocytes in the circulating blood, consequently eliminating canser growth.

Harringtonine and Homoharringtonine, hereinafter referred to as HH, has been known to be effective against acute chronic granulocytic and monocytic leukemia (Journal of Chinese Internal Medicine 3: 162–164, 1978). However, it has severe toxicity causing damage to heart and hematopoietic organs. The results of experiments in animals, such as mice, rabbits and dogs, indicate that most of them die from cardiotoxicity after receiving the drug. Therefore, there is a need to improve the HH drug for safe use against leukemia. This drug is of special importance in that all known antileukemia drugs are effective against lymphatic leukemia and there are no effective drugs for treating nonlymphatic leukemia. The pharmaseutical composition in accordance with the present invention treats nonlymphatic leukemia, especially acute chronic granulocytic and monocytic leukemia, without side effect.

SUMMARY OF THE INVENTION

A new improved pharmaceutical composition in accordance with the present invention named SAL for Safe Anti-Leukemia which comprises five major ingredients, namely Harringtonine, Homoharringtonine, Anethole, Oleanolic Acid and Ginsenoside and the method of making the same.

DETAILED DESCRIPTION OF THE INVENTION

It has been found that by addition of Anethole, Oleanolic Acid and Ginsenoside to the HH, a new composition is obtained which is effective in the treatment of nonlymphatic leukemia and which does not have the adverse side effects of HH.

The invention will be described with each component, as to its production, chemical structure and properties.

Throughout the specification, the concentration of the solvent is the same as first given unless stated otherwise. Reduced pressure means about 17 mm Hg. abs. l is liter, Kg is kilogram. ml if milliliter. Yield in weight %.

EXAMPLE 1

HH is extracted from the skins, stems, leaves and seeds of *Cephalotaxus fortunei* Hook and other related species, such as *Cephalotaxus sinensis* Li, *C. hainanensis*, and *C. wilsoniana*, including *C. oliveri* mast and *C. harringtonia*.

1 kg. of finely ground *Cephalotaxus fortunei* Hook is extracted with 8 l. of 90% ethanol at room temperature for 24 hrs. Filter the solution to yield a filtrate A and filtercake. Percolate the filtercake with ethanol and filter again to yield filtrate B. Combine A and B, and distill under reduced pressure to recover ethanol and an aqueous residue. To this residue, add 2% HCl to adjust the pH to 2.5. Separate the solids from the solution by filtration to yield a filtrate C. Wash the solids once with 2% HCl and filter to yield a filtrate D. Combine C and D to adjust the pH to 9.5 by adding saturated sodium carbonate solution. Extract the alkaline filtrate with chloroform and separate the chloroform layer from the aqueous layer. Repeat this extraction process five times. Combine all the chloroform extracts and distill at reduced pressure to recover chloroform and alkaloid as a solid residue respectively.

The solid alkaloid is then dissolved in 20 ml. of 6% citric acid in water. The solution is divided into three equal portions. These are adjusted to pH 7, 8 and 9 by adding saturated sodium carbonate solution.

The portions having pH 8 and 9 are combined and extracted with chloroform. The chloroform extracts are distilled under reduced pressure, whereby chloroform is removed and recovered and a solid residue of crude Harringtonine is obtained.

The crude Harringtonine is dissolved in pure ethanol i.e. alkaloid:anhydrous ethanol 1:10, and crystallized. The crystals are refined by recrystallization in diethyl ether. Overall yield of Harringtonine is about 0.1% including yield from mixed HH from subsequent process.

Harringtonine has the following chemical structure:

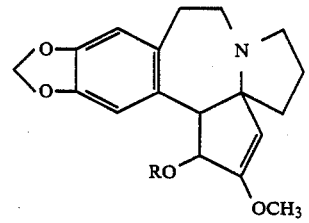

wherein R is 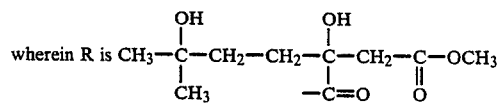

melting point: 135°–137° C.

crystal: colorless.

infrared spectrum: 3750, 1660, 1505, 1490, 1050, and 945 cm$^{-1}$.

ultraviolet spectrum: $\lambda_{peak}{}^{alcohol}$ mμ (log ε): 244 (3.59), 290 (3.65).

The portion having a pH of 7 and the mother liquors from the foregoing crystallization of Harringtonine are combined and passes through a liquid chromatographic column packed with alumina of diameter to height 1:50. The column is finally flushed with chloroform and followed by chloroform-methanol of 9:1 mixture. The resulting alkaloids are mixture of HH. The mixed HH is then separated from each other by countercurrent distribution employing chloroform and pH 5 buffer. The first fraction of the countercurrent distribution is Homoharringtonine and the last fraction of the countercurrent distribution is Harringtonine. Homoharringtonine is purified by crystallization in methyl alcohol. Homoharringtonine has the following chemical structure:

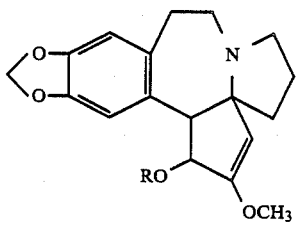

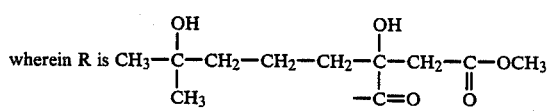

yield: 0.02%.

melting point: 144°–146° C.

infrared spectrum: 3500, 3400, 1665, 1030 and 940 cm$^{-1}$.

ultraviolet spectrum: $\lambda_{peak}^{ethanol}$ mμ (log ε): 240 (3.55), 290 (3.61).

EXAMPLE 2

Anethole, p-allyl-methoxy benzene, is extracted from Fennel, or Foeniculum Vulgare Mill. Extract 1 kg. of grated Fennel with 3 l. of 95% ethanol at room temperature for 24 hrs. Ethanol is recovered by distillation under reduced pressure from the ethanol extract and a residue containing crude anethole is dissolved in 1 l. of distilled water. This aqueous solution is distilled under reduced pressure whereby Fennel oil is distilled over with stream. Crude Fennel oil is separated from water and extracted with equal volume of diethyl ether. The ether extract is distilled under reduced pressure thereby recovering the diethyl ether and a residue of Fennel oil respectively. Yield of this crude Fennel oil is about 5.5%.

The resulting Fennel oil is fractionated with reflux on an oil bath. The fraction collected at a distilling temperature from 229°–237° C. is anethole.

overall yield: 3.3%.

Anethole has the following chemical structure:

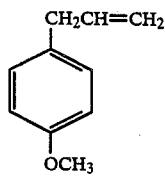

Anethole has a light yellow color.

specific gravity: at 25/25° 0.983–0.987.

refractive index at 25°: 1.588–1.561.

EXAMPLE 3

Oleanolic acid is extracted from fruits of *Ligustrum lucidum* Ait, *Hemsleys amabilis* Diels or *Sweritia milensis*. Extract 1 Kg. of the ground fruits of *Ligustrum lucidum* Ait. with 8 l. of 95% of ethanol at room temperature for 24 hrs. Separate residue from filtrate by filtration. Reflux the residue on water bath with 3 l. of 95% ethanol for 6 hrs. and collect filtrate. Repeat the reflux process once and combine both filtrates. Distill the filtrates under a reduced pressure to recover ethanol and a solid residue. Wash the residue with 1 l. of 60° C. distilled water. Filter the slurry and recover the solids. Dissolved the solids in ethanol and adjust the pH to 11 by adding sodium hydroxide solution. Filter and to the filtrate, add HCl until the pH is 1. Separate the crystal from the mother liquor. Concentrate the mother liquor to yield more crystal. Collect all the raw crystals and wash them with boiling sodium hydroxide solution of pH 11 and filter. To the crystals, add distilled water and filter. Dissolve the crystals in ethanol and adjust the pH to 1 by addition of HCl solution. A purified crystal of Oleanolic acid is obtained, after repeatedly washing the crystals with distilled water till the wash water is neutral.

yield: 0.65%

Oleanolic acid has the following chemical structure:

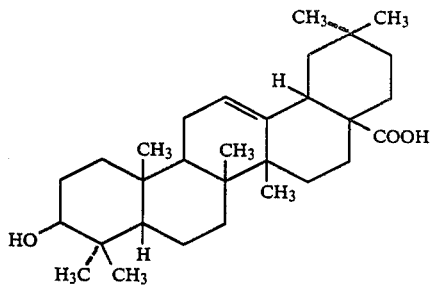

crystal: needle.

melting point: 310° C.

specific rotation at 20°, +80° (CH$_3$OH).

EXAMPLE 4

Ginsenoside has been disclosed in copending application filed on Apr. 29, 1985 by the same inventor, Yaguang Liu for Pharmaceutical Composition Containing Pure San-Mai-Sen, now, issued Pat. 4,684,628, the disclosure, regarding ginsenoside therein is hereby incorporated by reference.

The composition of a new antileukemia drug effective against granulocytic and monocytic leukemia without cardiotoxicity and damage to hematopoietic organs comrises:

| | |
|---|---|
| Harringtonine | 0.05%–2.0% by weight |
| Homoharringtonine | 0.02%–1.0% by weight |
| Anethole | 10.0%–90.0% by weight |
| Oleanolic acid | 1.0%–50.0% by weight |
| Ginsenoside | 5.0%–50.0% by weight |

The dosage of the above for hamans would be:

| | |
|---|---|
| Harringtonine | 2.5 mg. |
| Homoharringtonine | 1.25 mg. |
| Anethol | 300 mg. |
| Oleanolic acid | 50 mg. |
| Ginsenoside | 100 mg. |

The above composition can be manufactured in capsule, tablet or syrup form including ampule for injection according to prevalent art.

Now the invention will be further described with reference to its beneficial effects as illustrated by the following experiment test. It is noted that Avdin-Biotin-Peroxidase complex, known as ABC in immunoperoxidase technics is used. This technique is widely accepted because of its high sensitivity to the reaction with antigen.

Following is the result of an experiment using ABC technique in studying the effect of the above composition on the survival rate of chicken myocardial cells.

|  | survival rate of chicken myocardial cells (living/total) × 100, % | |
| --- | --- | --- |
| control | 92.0 ± 4.1 | (*10) |
| HH (10μ) | 61.2 ± 3.4 | (*20) |
| SAL (HH, 10μ + remainder 150μ) | 91.4 ± 4.0 | (*20) |
|  | P < 0.001 | |

*indicate number of samples

HH ampule or vial for injection contains
  Harringtonine 2.5 mg.
  Homoharringtonine 1.25 mg.
$LD_{50}$ of HH in accordance with the above formula in mice was 4.01±0.28 mg./kg of body weight.
$LD_{50}$ of SAL in accordance with human dosage in mice was 1005 mg./kg. of body weight.
$LD_{50}$ is the median lethal dosage.

From the above results, it is evident that the new drug according to the present invention is much safer than HH alone.

Numerous modifications and variation of the present invention are possible in light of the above teachings, and therefore, within the scope of the appended claims; the invention may be practiced otherwise than as particularly described.

What is claimed is:

1. A process for producing Oleanolic acid comprising
   a. extracting ground fruits of a plant selected from a group consising of *Ligustrum lucidum* Ait, *Hemsleys amabilis* Diels and *Sweritia milensis* with 95% ethanol at room temperature for 24 hrs;
   b. separating the ground fruits from the filtrate;
   c. refluxing twice the ground fruits with fresh 95% ethanol for 6 hrs to yield filtrates;
   d. combining filtrates from steps b and c and distilling the filtrates under reduced pressure to yield a solid residue;
   e. dissolving the solids in ethanol and adjusting the pH to 11;
   f. filtering and adjusting pH to 1; and
   g. crystallizing the Oleanolic acid, separating and washing the crystal repeatedly with water till the wash water is neutral.

2. A pharmaceutical product, produced according to the process of claim 1 having an effective anti-leukemia activity.

* * * * *